(12) United States Patent
Mower (10) Patent No.: US 7,203,537 B2
(45) Date of Patent: Apr. 10, 2007

(54) SYSTEM AND METHOD FOR BREAKING REENTRY CIRCUITS BY COOLING CARDIAC TISSUE

(75) Inventor: Morton M. Mower, Baltimore, MD (US)

(73) Assignee: MR3 Medical, LLC, North Oaks, MN (US)

( * ) Notice: Subject to any disclaimer, the term of this patent is extended or adjusted under 35 U.S.C. 154(b) by 148 days.

(21) Appl. No.: 10/754,887

(22) Filed: Jan. 10, 2004

(65) Prior Publication Data

US 2004/0167581 A1 Aug. 26, 2004
US 2006/0241707 A9 Oct. 26, 2006

Related U.S. Application Data

(63) Continuation-in-part of application No. 09/929,478, filed on Aug. 14, 2001, now Pat. No. 6,895,274, which is a continuation of application No. 09/231,570, filed on Jan. 14, 1999, now Pat. No. 6,295,470, which is a continuation-in-part of application No. 08/699,552, filed on Aug. 19, 1996, now Pat. No. 5,871,506, application No. 10/754,887, which is a continuation-in-part of application No. 10/053,750, filed on Jan. 21, 2002, which is a continuation of application No. 09/690,947, filed on Oct. 18, 2000, now Pat. No. 6,341,235, which is a continuation-in-part of application No. 09/008,636, filed on Jan. 16, 1998, now Pat. No. 6,136,019, which is a continuation-in-part of application No. 08/699,552, filed on Aug. 19, 1996, now Pat. No. 5,871,506.

(60) Provisional application No. 60/439,206, filed on Jan. 10, 2003.

(51) Int. Cl.
*A61N 1/37* (2006.01)

(52) U.S. Cl. .......................................................... 607/3
(58) Field of Classification Search .................... 607/3, 607/14
See application file for complete search history.

(56) References Cited

U.S. PATENT DOCUMENTS

| 3,924,641 A | 12/1975 | Weiss |
| 3,946,745 A | 3/1976 | Siang-Lai et al. |
| 4,010,758 A | 3/1977 | Rockland et al. |

(Continued)

FOREIGN PATENT DOCUMENTS

EP 0 491 649 9/1996

(Continued)

OTHER PUBLICATIONS

Guyton, Textbook of Medical Physiology, 8th Edition, Chapter 9, pp. 98-99, 1991.

(Continued)

*Primary Examiner*—Scott M. Getzow
(74) *Attorney, Agent, or Firm*—Roberts Mardula & Wertheim, LLC (57) ABSTRACT

Systems and methods to inhibit the conduction of certain spurious electrical impulses in the heart. Inhibition of spurious electrical impulses in the heart is accomplished by cooling one or more targeted portions of the heart. Optionally, inhibition of spurious electrical impulses may be accomplished by cooling of cardiac tissue in combination with pacing of the heart.

58 Claims, 5 Drawing Sheets

U.S. PATENT DOCUMENTS

| | | |
|---|---|---|
| 4,019,519 A | 4/1977 | Geerling |
| 4,055,190 A | 10/1977 | Tany |
| 4,222,386 A | 9/1980 | Smolnikov et al. |
| 4,233,986 A | 11/1980 | Tannenbaum |
| 4,298,007 A | 11/1981 | Wright et al. |
| 4,327,322 A | 4/1982 | Yukl |
| 4,343,312 A | 8/1982 | Cals et al. |
| 4,392,496 A | 7/1983 | Stanton |
| 4,402,322 A | 9/1983 | Duggan |
| 4,429,697 A | 2/1984 | Nappholz et al. |
| 4,444,195 A | 4/1984 | Gold |
| 4,456,012 A | 6/1984 | Lattin |
| 4,481,953 A | 11/1984 | Gold et al. |
| 4,498,478 A | 2/1985 | Bourgeois |
| 4,503,857 A | 3/1985 | Boute et al. |
| 4,539,991 A | 9/1985 | Boute et al. |
| 4,543,956 A | 10/1985 | Herscovici |
| 4,545,956 A | 10/1985 | Ciszewski et al. |
| 4,569,350 A | 2/1986 | Mumford et al. |
| RE32,091 E | 3/1986 | Stanton |
| 4,612,934 A | 9/1986 | Borkan |
| 4,637,397 A | 1/1987 | Jones et al. |
| 4,646,744 A | 3/1987 | Capel |
| 4,662,377 A | 5/1987 | Heilman et al. |
| 4,723,552 A | 2/1988 | Kenyon et al. |
| 4,729,376 A | 3/1988 | DeCote, Jr. |
| 4,754,759 A | 7/1988 | Allocca |
| 4,781,194 A | 11/1988 | Elmqvist |
| 4,821,724 A | 4/1989 | Whigham et al. |
| 4,823,810 A | 4/1989 | Dervieux |
| 4,875,484 A | 10/1989 | Anzai et al. |
| 4,903,700 A | 2/1990 | Whigham et al. |
| 4,919,140 A | 4/1990 | Borgens et al. |
| 4,924,880 A | 5/1990 | O'Neill et al. |
| 4,940,054 A | 7/1990 | Grevis et al. |
| 4,944,298 A | 7/1990 | Sholder |
| 4,976,264 A | 12/1990 | Petrofsky |
| 4,989,605 A | 2/1991 | Rossen |
| 4,996,987 A | 3/1991 | Petrofsky |
| 5,018,522 A | 5/1991 | Mehra |
| 5,027,815 A | 7/1991 | Funke et al. |
| 5,036,850 A | 8/1991 | Owens |
| 5,048,522 A | 9/1991 | Petrofsky |
| 5,052,391 A | 10/1991 | Silberstone et al. |
| 5,058,584 A | 10/1991 | Bourgeois |
| 5,063,929 A | 11/1991 | Bartelt et al. |
| 5,065,083 A | 11/1991 | Owens |
| 5,069,211 A | 12/1991 | Bartelt et al. |
| 5,083,564 A | 1/1992 | Scherlag |
| 5,097,833 A | 3/1992 | Campos |
| 5,105,810 A | 4/1992 | Collins et al. |
| 5,109,847 A | 5/1992 | Liss et al. |
| 5,111,811 A | 5/1992 | Smits |
| 5,117,826 A | 6/1992 | Bartelt et al. |
| 5,156,147 A | 10/1992 | Warren et al. |
| 5,163,429 A | 11/1992 | Cohen |
| 5,181,511 A | 1/1993 | Nickolls et al. |
| 5,193,535 A | 3/1993 | Bardy et al. |
| 5,205,284 A | 4/1993 | Freeman |
| 5,209,229 A | 5/1993 | Gilli |
| 5,213,098 A | 5/1993 | Bennett et al. |
| 5,215,083 A | 6/1993 | Drane et al. |
| 5,224,475 A | 7/1993 | Berg et al. |
| 5,224,476 A | 7/1993 | Ideker et al. |
| 5,233,985 A | 8/1993 | Hudrlik |
| 5,292,340 A | 3/1994 | Crosby et al. |
| 5,300,096 A | 4/1994 | Hall et al. |
| 5,314,423 A | 5/1994 | Seney |
| 5,314,495 A | 5/1994 | Kovacs |
| 5,318,591 A | 6/1994 | Causey, III et al. |
| 5,332,401 A | 7/1994 | Davey et al. |
| 5,334,220 A | 8/1994 | Sholder |
| 5,340,361 A | 8/1994 | Sholder |
| 5,350,401 A | 9/1994 | Levine |
| 5,391,185 A | 2/1995 | Kroll |
| 5,411,525 A | 5/1995 | Swanson et al. |
| 5,411,547 A | 5/1995 | Causey, III |
| 5,417,718 A | 5/1995 | Kleks et al. |
| 5,421,830 A | 6/1995 | Epstein et al. |
| 5,422,525 A | 6/1995 | Mansir |
| 5,423,868 A | 6/1995 | Nappholz et al. |
| 5,441,522 A | 8/1995 | Schuller |
| 5,458,619 A | 10/1995 | Olson |
| 5,458,625 A | 10/1995 | Kendall |
| 5,468,254 A | 11/1995 | Hahn et al. |
| 5,480,413 A | 1/1996 | Greenhut et al. |
| 5,487,759 A | 1/1996 | Bastyr et al. |
| 5,507,781 A | 4/1996 | Kroll et al. |
| 5,514,161 A | 5/1996 | Limousin |
| 5,514,162 A | 5/1996 | Bornzin et al. |
| 5,514,163 A | 5/1996 | Markowitz et al. |
| 5,522,858 A | 6/1996 | van der Veen |
| 5,527,347 A | 6/1996 | Shelton et al. |
| 5,534,015 A | 7/1996 | Kroll et al. |
| 5,534,018 A | 7/1996 | Wahlstrand et al. |
| 5,540,730 A | 7/1996 | Terry et al. |
| 5,545,186 A | 8/1996 | Olson et al. |
| 5,549,652 A | 8/1996 | McClure et al. |
| 5,562,708 A | 10/1996 | Combs et al. |
| 5,571,143 A | 11/1996 | Hoegnelid et al. |
| 5,584,868 A | 12/1996 | Salo et al. |
| 5,601,608 A | 2/1997 | Mouchawar |
| 5,601,611 A | 2/1997 | Fayram et al. |
| 5,601,615 A | 2/1997 | Markowitz et al. |
| 5,620,470 A | 4/1997 | Gliner et al. |
| 5,620,471 A | 4/1997 | Duncan |
| 5,626,620 A | 5/1997 | Kieval et al. |
| 5,649,966 A | 7/1997 | Noren et al. |
| 5,651,378 A | 7/1997 | Matheny et al. |
| 5,658,319 A | 8/1997 | Kroll |
| 5,662,698 A | 9/1997 | Altman et al. |
| 5,674,253 A | 10/1997 | Adams et al. |
| 5,683,431 A | 11/1997 | Wang |
| 5,690,691 A | 11/1997 | Chen et al. |
| 5,697,953 A | 12/1997 | Kroll et al. |
| 5,713,924 A | 2/1998 | Min et al. |
| 5,713,929 A | 2/1998 | Hess et al. |
| 5,718,720 A | 2/1998 | Prutchi et al. |
| 5,735,876 A | 4/1998 | Kroll et al. |
| 5,741,303 A | 4/1998 | Kroll et al. |
| 5,800,464 A | 9/1998 | Kieval |
| 5,800,465 A | 9/1998 | Thompson et al. |
| 5,814,079 A | 9/1998 | Kieval |
| 5,836,994 A | 11/1998 | Bourgeois |
| 5,855,592 A | 1/1999 | McGee et al. |
| 5,855,594 A | 1/1999 | Olive et al. |
| 5,871,506 A | 2/1999 | Mower |
| 5,871,560 A | 2/1999 | Fluch et al. |
| 5,876,422 A * | 3/1999 | van Groeningen ............ 607/3 |
| 5,968,081 A | 10/1999 | Levine |
| 6,026,326 A | 2/2000 | Bardy |
| 6,067,470 A | 5/2000 | Mower |
| 6,136,019 A | 10/2000 | Mower |
| 6,141,586 A | 10/2000 | Mower |
| 6,141,587 A | 10/2000 | Mower |
| 6,178,351 B1 | 1/2001 | Mower |
| 6,216,039 B1 | 4/2001 | Bourgeois |
| 6,223,072 B1 | 4/2001 | Mika et al. |
| 6,248,126 B1 * | 6/2001 | Lesser et al. ............... 607/113 |
| 6,263,242 B1 | 7/2001 | Mika et al. |
| 6,292,693 B1 | 9/2001 | Darvish et al. |
| 6,317,631 B1 | 11/2001 | Ben-Haim et al. |
| 6,360,126 B1 | 3/2002 | Mika et al. |
| 6,363,279 B1 | 3/2002 | Ben-Haim et al. |

| | | |
|---|---|---|
| 6,370,430 B1 | 4/2002 | Mika et al. |
| 6,424,866 B2 | 7/2002 | Mika et al. |
| 6,571,127 B1 | 5/2003 | Ben-Haim et al. |
| 6,597,952 B1 | 7/2003 | Mika et al. |
| 6,947,792 B2 | 9/2005 | Ben-Haim et al. |
| 2003/0014097 A1 | 1/2003 | Putz et al. |
| 2004/0158289 A1 | 8/2004 | Girouard et al. |

FOREIGN PATENT DOCUMENTS

| | | |
|---|---|---|
| EP | 0 813 889 | 12/1997 |
| EP | 0 850 662 | 7/1998 |
| EP | 0 870 516 | 10/1998 |
| EP | 0 600 631 | 12/1999 |
| FR | 2763247 | 5/1997 |
| WO | 93/01861 | 2/1993 |
| WO | WO-97/13547 A1 | 4/1997 |
| WO | 97/25098 | 7/1997 |
| WO | 99/36124 | 7/1997 |
| WO | 99/61101 | 12/1999 |
| WO | 00/01443 | 1/2000 |

OTHER PUBLICATIONS

Brian G. Cleland, "A Conceptual Basis for Pacing Waveforms," Pace, vol. 19, 1177-1185 (Aug. 1996).

Allen M. Greenspan, M.D., "Electrophysiology of Pacing," 29-35, Ideal Cardiac Pacing, vol. 37 in the Series, Major Problems in Clinical Surgery (1984).

Brian F. Hoffman, M.D., and Paul F. Cranefield, M.D., Electrophysiology of the Heart, 220-222, (1976).

Bradley J. Roth, Ph.D., "Strength-Internal Curves for Cardiac Tissue Predicted Using the Bidomain Model," Journal of Cardiovascular Electrophysiology, vol. 7, No. 8, 722-737 (Aug. 1996).

Harold Siddons and Edgar Sowton, "Cardiac Pacemakers," 152-154.

Estes et al., Implantable Cardioverter-Defibrillators, p. 181 (1994).

Willems, Rik; Sipido, Karin R. "Nonexcitatory stimulation as a novel treatment for heart failure: cause for excitement?" European Heart Journal (2004) 25, 626-628 (Elsevier Ltd. on behalf of European Society of Cardiology).

Khaykin, Yaariv; Saad, Eduardo B.; Wilkoff, Bruce L. "Pacing in heart failure: The benefit of resynchronization." Cleveland Clinic Journal of Medicine, Oct. 2003, pp. 841-865, vol. 70 No. 10.

Stix, Guenter, et al. "Chronic electrical stimulation during the absolute refractory period of the myocardium improves severe heart failure." European Heart Journal (2004) 25, 650-655 (Elsevier Ltd. on behalf of European Society of Cardiology).

Euler De, Scanlon PJ. "Acetylcholine Release by a Stimulus Train Lowers Atrial Fibrillation Threshold," AM J Physiol. Oct. 1987. ;253(4 pt 2):H863-8.

Zilberter YI, Starmer CF, Grant AO. Open Na+ Channel Blockade: Multiple Rest States Revealed by Channel Interactions with Disopyramide and Quinidine, + Am J Physiol. May 1994;266(5 pt 2):H2007-17.

Nice Acropolis, Archives Des Maladies du Coeur et des Vaisseaux, Journal D'Expression de la Societe Francaise de Cardiologie; (Jun., 1998).

Lorente P, Delgado C, Delmar M, Henzel D, Jalife J., "Hysteresis in the Excitability of Isolated Guinea Pig Ventricular Myocytes,"Circ Res. Nov. 1991;69(5):1301-15.

* cited by examiner

SYSTEM AND METHOD FOR BREAKING REENTRY CIRCUITS BY COOLING CARDIAC TISSUE

CROSS REFERENCE TO RELATED APPLICATIONS

This application is a continuation-in-part of U.S. patent application Ser. No. 09/929,478 filed Aug. 14, 2001, now U.S. Pat. No. 6,895,274, which is a continuation of U.S. Ser. No. 09/231,570 application filed Jan. 14, 1999, now U.S. Pat. No. 6,295,470, which is a continuation-in-part of U.S. patent application Ser. No. 08/699,552, filed Aug. 19, 1996, now U.S. Pat. No. 5,871,506 and a continuation-in-part of U.S. patent application Ser. No. 10/053,750 filed Jan. 21, 2002, pending, which is a continuation of U.S. patent application Ser. No. 09/690,947, filed Oct. 18, 2000, now U.S. Pat. No. 6,341,235, which is a continuation-in-part of U.S. patent application Ser. No. 09/008,636 filed Jan. 16, 1998, now U.S. Pat. No. 6,136,019, which is a continuation-in-part of U.S. patent application Ser. No. 08/699,552, filed Aug. 19, 1996, now U.S. Pat. No. 5,871,506. This application claims priority under 35 U.S.C. § 119(e) from provisional application No. 60/439,206 filed Jan. 10, 2003. The Ser. Nos. 09/929,478, 10/053,750, and 60/387,517 applications, as well as the U.S. Pat. Nos. 6,295,470 and 6,341,235 Patents, are all incorporated by reference herein, in their entireties, for all purposes.

INTRODUCTION

The present invention relates generally to a system and method for the stimulation of cardiac muscle tissue. In particular, the embodiments of the present invention provide a system and method for treating cardiac tissue by cooling the cardiac tissue to inhibit the conduction of certain electrical signals in cardiac tissue and decrease the duration of tachycardia and enhance the effects of pacing and defibrillation stimuli.

BACKGROUND

The function of the cardiovascular system is vital for survival. Through blood circulation, body tissues obtain necessary nutrients and oxygen, and discard waste substances. In the absence of circulation, cells begin to undergo irreversible changes that lead to death. The muscular contractions of the heart are the driving force behind circulation.

Each of the heart's contractions, or heartbeats, is triggered by electrical impulses. These electrical impulses are sent from the sinoatrial node (the heart's natural pacemaker), which is located at the top of the upper-right chamber of the heart or right atrium. From there, the electrical impulses travel through the upper chambers of the heart (atria) and to the atrioventricular (AV) node, where they are transmitted to the lower chambers of the heart ventricles via the "bundle branches." Thus, the electrical impulses travel from the sinoatrial node to the ventricles, to trigger and regulate the heartbeat.

An arrhythmia is an abnormal heartbeat resulting from any change, deviation or malfunction in the heart's conduction system—the system through which normal electrical impulses travel through the heart. Under normal conditions, each of the heart's contractions, or heartbeats, is triggered by electrical impulses. These electrical impulses are sent from the sinoatrial node (the heart's natural pacemaker), which is located at the top of the upper-right chamber of the heart or right atrium. From there, the electrical impulses travel through the upper chambers of the heart (atria) and to the atrioventricular (AV) node, where they are transmitted to the lower chambers of the heart ventricles via the "bundle branches." Thus, the electrical impulses travel from the sinoatrial node to the ventricles, to trigger and regulate the heartbeat.

When the electrical "circuits" of the heart do not operate optimally, an arrhythmia may result. An arrhythmia may result in unusually fast (tachycardia) or unusually slow (bradycardia) heartbeats. The cause of an arrhythmia may be related to a previous heart condition (e.g., previous damage from a heart attack) or to other factors (e.g., drugs, stress, not getting enough sleep). In the majority of cases, a skipped beat is not medically significant. The most serious arrhythmias, however, contribute to approximately 500,000 deaths in the United States each year according to the American Heart Association. Sudden cardiac death ("cardiac arrest") is responsible for approximately one-half of all deaths due to heart disease, and is the number one cause of death in the US, according to the North American Society of Pacing and Electrophysiology.

Almost all clinically important tachyarrhythmias are the result of a propagating impulse that does not die out but continues to propagate and reactivate cardiac tissue (referred to as "reentry"). Such tachyarrhythmias include sinus node reentry, atrial fibrillation, atrial flutter, atrial tychycardia, AV nodal reentry tachycardia, AV reentry (Wolff-Parkinson-White syndrome or concealed accessory AV connection), ventricular tachycardia, and bundled branch reentrant tachycardia.

For reentry to occur, there must exist a substrate in the cardiac tissue capable of supporting reentry (the "reentry circuit"). The activation wave front must be able to circulate around a central area of block and encounter a unidirectional block such that it is forced to travel in one direction around the central block. (If the activation wave front is permitted to travel in both directions around the block, the wave fronts will collide and die out.) Of importance is the conductance speed of the circulating wave front. If the conductance speed is too fast, the circulating wave front will arrive at its point of origin before the tissue has repolarized sufficiently to become excitable again. Thus, at least one area of slow conductance is part of the reentry circuit for virtually all clinical reentrant rhythms. Eliminating the slow conductance elements of a reentry circuit destroys the circuit.

Atrial fibrillation (AF) is the most common type of sustained arrhythmia, affecting two million people each year in the United States alone. Both atrial fibrillation and atrial flutter increase the risk of stroke. According to the American Heart Association, they lead to over 54,000 deaths in the United States each year. The risk of developing atrial fibrillation increases dramatically with age. As a result, approximately 70 percent of patients with atrial fibrillation are between the ages of 65 and 85 years old. AF is a rapid, abnormal heart rhythm (arrhythmia) caused by faulty electrical signals from the upper chambers of the heart (atria). Electrical signals should normally be coming only from the sinoatrial node in a steady rhythm—about 60 to 100 beats per minute. A heart experiencing AF presents two heart rates—an atrial rate and a heart rate. With AF, the atrial rate is 300–400 beats per minute while the heart rate is 100–175 beats per minute. This heart rate is the result of the AV node blocking out most of the atrial impulses, and allowing only the fewer impulses to emerge to the ventricle.

Certain arrhythmias are related to specific electrical problems within the heart. AV nodal reentrant tachycardia is an arrhythmia caused by an extra conducting pathway within the AV node. This allows the heart's electrical activity to "short circuit" or recyle within the AV nodal region.

AV reentrant tachycardia results from an extra conducting pathway that allows the electrical impulse to "short circuit" and bypass the AV node altogether. In this mode, the extra "circuit" directly links the atria and ventricles. In most cases, this pathway can only conduct "backwards"—from ventricles to atria. This is called a "concealed accessory pathway" since it cannot be diagnosed from a regular electrocardiogram (EKG). These arrhythmias may be treated medically, but can also be cured by catheter ablation. Less often, the extra pathway conducts in the forward direction (from atrium to ventricle) and is evident on the EKG, in which case the condition is called the Wolff-Parkinson-White syndrome (WPW). WPW syndrome may result in extremely rapid heartbeats and could potentially result in death. Symptomatic WPW syndrome generally requires catheter ablation.

A quite different (and life threatening) condition is ventricular fibrillation. Ventricular fibrillation involves a quivering of the ventricles instead of the atria. Unlike AF, it is life threatening because it results in 350 beats per minute or higher. The heart cannot keep that rate up for more than a few minutes without treatment (e.g., with a defibrillator).

Under some conditions, arrhythmias may be transient. For example, a patient may be experiencing a particular period of stress, an illness, or a drug (legal or otherwise) reaction. In other cases, more invasive treatments are helpful. For a slow heartbeat (bradycardia), the most common treatment is an electronic (artificial) pacemaker. This device, which is implanted under the skin and permanently attached to the heart, delivers an electrical impulse when a slowing or irregularity of the heart rhythm is detected. For abnormally fast heartbeat rates, an implantable cardioverter defibrillator (ICD) may be implanted. An ICD monitors and, if necessary, corrects an abnormally fast heartbeat. These devices may be lifesaving for patients with ventricular fibrillation or ventricular tachycardia. Another procedure is an electrophysiology study with catheter ablation. This is a procedure in which catheters are introduced into the heart from blood vessels in the legs and/or neck and radio frequency energy is used to very carefully destroy (ablate) the abnormal areas of the heart that are creating the arrhythmias.

In cardiac muscle, the muscle fibers are interconnected in branching networks that spread in all directions through the heart. When any portion of this net is stimulated, a depolarization wave passes to all of its parts and the entire structure contracts as a unit. Before a muscle fiber can be stimulated to contract, its membrane must be polarized. A muscle fiber generally remains polarized until it is stimulated by some change in its environment. A membrane can be stimulated electrically, chemically, mechanically or by temperature change. The minimal stimulation strength needed to elicit a contraction is known as the threshold stimulus. The maximum stimulation amplitude that may be administered without eliciting a contraction is the maximum subthreshold amplitude.

Throughout much of the heart are clumps and strands of specialized cardiac muscle tissue. This tissue comprises the cardiac conduction system and serves to initiate and distribute depolarization waves throughout the myocardium. Any interference or block in cardiac impulse conduction may cause an arrhythmia or marked change in the rate or rhythm of the heart.

Biphasic—either cathodal or anodal—current may be used to stimulate the myocardium. However, until the work embodied in U.S. Pat. Nos. 5,871,506 and 6,141,586 for example, anodal current was thought not to be useful clinically. Cathodal current comprises electrical pulses of negative polarity. This type of current depolarizes the cell membrane by discharging the membrane capacitor, and directly reduces the membrane potential toward threshold level. Cathodal current, by directly reducing the resting membrane potential toward threshold has a one-half to one-third lower threshold current in late diastole than does anodal current. Anodal current comprises electrical pulses of positive polarity. Presently, virtually all artificial pacemaking is done using stimulating pulses of negative polarity although the utility of anodal pulse has been demonstrated.

The typical implantable cardioverter/defibrillator (ICD) delivers an initial electrical countershock within ten to twenty seconds of arrhythmia onset, thereby saving countless lives. Improved devices have antitachycardia pacing capabilities in addition to cardioverting/defibrillating functions. These ICDs are capable of different initial responses to one or more tachycardia as well as a programmable sequence of responses to a particular arrhythmia.

The output energy level is generally set by a physician in accordance with a patient's capture threshold, determined at the time of heart implantation. This threshold represents the minimum pacing energy required to reliably stimulate a patient's heart. However, due to trauma associated with the stimulation, scar tissue grows at the interface between the implanted cardiac pacer leads and the myocardium. This scar tissue boosts the patient's capture threshold. To insure reliable cardiac capture, the output energy level is thus generally set at a level which is a minimum of two times greater than the initially measured capture threshold. A drawback to such an approach is that the higher stimulation level causes more trauma to the cardiac tissue than would a lower level of stimulation, and hence promotes the formation of scar tissue, thereby boosting the capture threshold. The higher stimulation level also shortens battery life. This is not desirable, as a shorter battery life necessitates more frequent surgery to implant fresh batteries.

Another drawback is the potential for patient discomfort associated with this higher stimulation level. This is because the higher stimulation level can stimulate the phrenic or diaphragmatic plexus or cause intercostal muscle pacing. Lastly, the higher stimulation is less effective, due to entry block.

Improvements to pacing technology have resulted in an enhanced conduction of electrical pulses associated with resultant heartbeats for those arrhythmia victims who do not respond to ordinary pacing. For example U.S. Pat. No. 6,343,232 B1 entitled "Augmentation of Muscle Contractility by Biphasic Stimulation" was issued to Morton M. Mower M.D. That invention described increasing electrical conduction and contractility by biphasic pacing comprising an initial anodal pulse followed by a cathodal pulse. This technique increased the speed of conduction of the resultant beats by almost 100% over that produced by conventional pacing stimuli. However, this technique did not result in reversion to a sinus rhythm for all victims of cardiac conduction disorder.

What would be truly useful is to provide alternative methods of stimulating the myocardium and to inhibit the conduction of certain spurious electrical impulses in the heart as a substitution for, or as an enhancement to, conventional pacing and pharmaceutical therapies and/or to use the alternative method in conjunction with conventional pacing and safe pharmaceuticals to provide yet another method for overcoming cardiac conduction problems.

SUMMARY

An embodiment of the present invention comprises an implantable cardiac treatment/stimulation device designed to inhibit the conduction of certain spurious electrical impulses preferably without pacing. The technique applied in the implantable device comprises a cooling element for cooling cardiac tissue. Optionally, the cooling process may be provided in combination with biphasic stimulation of the cardiac tissue.

It is therefore an aspect of the present invention to inhibit the conduction of certain spurious electrical impulses in cardiac tissue affected by re-entry circuits.

It is a further aspect of the present invention to inhibit the conduction of certain spurious electrical impulses in the heart by cooling cardiac tissue affected by re-entry circuits.

It is a further aspect of the present invention to selectively apply cold temperature to areas of the cardiac tissue to inhibit the conduction of certain spurious electrical impulses in cardiac tissue affected by re-entry circuits.

It is yet another aspect of the present invention to apply cold over large areas of the cardiac tissue to inhibit the conduction of certain spurious electrical impulses in cardiac tissue affected by re-entry circuits.

It is still another aspect of the present invention to affect reentry circuits in a more effective manner than conventional cardiac pacing.

It is still another aspect of the present invention to inhibit the conduction of certain spurious electrical impulses in the heart over large areas of tissue rather than only over small areas of a pacing site.

It is further aspect of the present invention to provide an implantable stimulation device for automatically applying cold to cardiac tissue affected by re-entry circuits.

It is yet another aspect of the present invention to provide a removable device for applying cold to cardiac tissue in operating room settings or trauma settings.

It is still another aspect of the present invention to provide an implantable device that combines cooling of cardiac tissue with stimulation of cardiac tissue through conventional pacing means.

It is another aspect of the present invention to provide an implantable device that combines cooling of cardiac tissue with stimulation of cardiac tissue through biphasic stimulation.

It is a further aspect of the present invention to provide an implantable cardiac stimulation device that can sense the onset of fibrillation or other tachyarrhythmias and can selectively apply cooling of cardiac tissue, pacing of cardiac tissue, defibrillation of cardiac tissue or a combination thereof as the situation dictates.

In one aspect of the invention, both cooling and biphasic electrical stimulation is administered to the cardiac muscle. The anodal stimulation component of biphasic electrical stimulation augments cardiac contractility by hyperpolarizing the tissue prior to excitation, leading to faster impulse conduction, more intracellular calcium release, and the resulting superior cardiac contraction. The cathodal stimulation component eliminates the drawbacks of anodal stimulation alone, resulting in effective cardiac stimulation at a lower voltage level than would be required with anodal stimulation alone. This in turn, extends pacemaker battery life and reduces tissue damage.

In a second aspect of the invention, cooling is applied to the cardiac tissue and biphasic electrical stimulation is administered to the cardiac blood pool, that is, the blood entering and surrounding the heart. This enables cardiac stimulation without the necessity of placing electrical leads in intimate contact with cardiac tissue, thereby diminishing the likelihood of damage to this tissue. The stimulation threshold of biphasic stimulation administered via the blood pool is in the same range as standard stimuli delivered directly to the heart muscle. Through the use of biphasic electrical stimulation to the cardiac blood pool it is therefore possible to achieve enhanced cardiac contraction, without skeletal muscle contraction, cardiac muscle damage or adverse effects to the blood pool.

Yet another embodiment of the present invention comprises an implantable device for automatic treatment of frequently recurring bouts of atrial fibrillation or chronic atrial fibrillation. This embodiment comprises a sensing system which monitors various parameters such as the PDF (probability density function) of the atrium to sense atrial fibrillation. By sensing the PDF of the atrium, this provides a detector for atrial fibrillation that has not been previously considered. Upon sensing the PDF of the atrium and determining that atrial fibrillation is occurring, the implantable device of the present invention initially applies cooling to the cardiac tissue of the atria. This cooling is applied across a broad area via contact device dimensional to cover an extensive area of cardiac tissue. The cold temperature is then applied over the contact device to the cardiac tissue, cooling the cardiac tissue, and thereby inhibiting the conduction of spurious signals through the tissue. This decreased temperature will affect the reentry circuits in an effective fashion. Since the intervention is applied to a large area of tissue rather than a small pacing site, the inhibition of spurious signals can be achieved over a much broader area than a single point of contact as in conventional pacing.

Cold is applied to the cardiac tissue for a brief period of time that is programmable and adjustable as sensors detect the need for the application of the cold. The amount of cooling applied and the total temperature of the heart are monitored through a thermostat function of the apparatus. Cooling can be accomplished by a mechanical hydraulic system for pumping cooled fluid into a bladder on the surface of the atrium.

The heart rhythm is monitored and the application of cold temperature is repeated a number of times if initially unsuccessful.

In those cases where the decrease of temperature of this embodiment alone fails to entrain the cardiac tissue, an alternative embodiment comprises both a cooling element in the form of a contact device and more conventional cardiac stimulation elements that apply an electrical pulse to the cardiac tissue in the form of a negative phase, as an anodal pulse followed by a negative pulse, or other stimulation method known in the art.

This combination of cooling of cardiac tissue combined with cardiac stimulation comprises yet another embodiment of the present invention. A processor in the implantable device senses the onset of fibrillation and first applies cold temperature to the cardiac tissue. If this fails to affect the reentry circuits of the heart, a combination of cooling and electrical stimulation and/or electrical stimulation alone could then be applied. If the combination does not affect the reentry circuit, then individual pacing in the more conventional fashion could be applied. Thus sensing and the application of stimulation of either cold temperature electrical stimulation or a combination thereof are provided by circuitry within the implantable device.

The application of the embodiments described above would not require anesthesia and would potentially have a higher effective rate than conventional cardio-version.

A further embodiment of the present invention involves connecting the implantable device to a communication terminal, preferably wireless, so that an appropriate caregiver can receive notice of a cardiac event. Signals could then be received by the physician indicating the condition. The physician would then have the option to remotely control the stimulation protocol applied by the implantable device of the present invention.

Yet another embodiment of the present invention involves altering the conductance of the heart by application of cold temperature with other forms of pacing such as rate control, and defibrillation. Pacing includes but is not limited to bipolar, biphasic, unipolar, monophasic, overdrive, atrial alone, atrio-ventricular and sequential pacing.

An embodiment of the present invention provides methods for inhibiting the conduction of spurious electrical impulses in cardiac tissue comprising establishing a temperature conducive to inhibited conduction of electrical impulses for a targeted portion of the heart; and applying a temperature decrease to the targeted portion to maintain the established temperature.

Another embodiment of the present invention provides methods for inhibiting the conduction of spurious electrical impulses in cardiac tissue. The method comprising sensing the onset of arrhythmia, determining the temperature of the cardiac tissue at the time of onset of arrhythmia, and applying a temperature decrease below the present temperature to the cardiac tissue.

Another embodiment of the present invention provides methods for inhibiting the conduction of spurious electrical impulses in cardiac tissue. A heat-transfer operator is situated at each of one or more targeted portions of the heart. In an embodiment of the present invention, the heat-transfer operator is a Peltier cooler. In another embodiment of the present invention, the heat-transfer operator is a heat sink that is thermally coupled to a Peltier cooler. A symptom associated with an arrhythmia is detected, and, in response to detection of the symptom, the heat is selectively transferred away from the targeted portion in the heart related to arrhythmia by absorbing heat into the heat-transfer operator situated at the targeted portion r.

In another embodiment of the present invention, methods for suppressing arrhythmia in a patient are provided. A heat-transfer operator is implanted at each of one or more targeted portions of a patient's heart. At least one heat-transfer operator is operated to cool at least one targeted portion of the heart, thereby suppressing the arrhythmia.

In still another embodiment of the present invention, methods are provided for inhibiting the conduction of spurious electrical impulses in cardiac tissue. The onset of arrhythmia is sensed and the sensed arrhythmia evaluated. The temperature of the cardiac tissue at the time of onset of arrhythmia is also determined. Based on the evaluation of the sensed arrhythmia and cardiac tissue temperature, one or more remedial measures is selected from the group consisting of applying a temperature decrease to the cardiac tissue and applying a pacing pulse to the cardiac tissue. The selected remedial measure is applied.

Another embodiment of the present invention comprises apparatuses for inhibiting the conduction of spurious electrical impulses in cardiac tissue. A sensing means senses the onset of arrhythmia. A cooling means responsive to the sensing means applies a cooling stimulus to the cardiac tissue. In yet another embodiment of the present invention, apparatuses are provided or inhibiting the conduction of spurious electrical impulses in cardiac tissue. A sensor detects a symptom associated with an arrhythmia. A heat-transfer operator is situated at each of one or more targeted portions of the heart. In an embodiment of the present invention, the heat-transfer operator is a Peltier cooler. In another embodiment of the present invention, the heat-transfer operator is a heat sink coupled to a Peltier cooler implanted in the torso of the patient. The heat-transfer operator at each of the one or more targeted portions is adapted to respond to the sensor to remove heat from the targeted portion served by that heat-transfer operator.

In still another embodiment of the present invention, apparatuses for suppressing arrhythmia in a patient are provided. A sensor detects a symptom associated with an arrhythmia. A heat-transfer operator is implanted at each of one or more targeted portions of a patient's heart. In response to the detection of arrhythmia, the heat-transfer operator at each of the one or more targeted portions is adapted to transfer heat away from the targeted portion served by that heat-transfer operator such that each of the one or more targeted portions is cooled and the arrhythmia is suppressed.

DETAILED DESCRIPTION

Embodiments of the present invention provide systems and methods for treating cardiac tissue by cooling the cardiac tissue to inhibit the conduction of certain electrical signals in cardiac tissue and decrease the duration of tachycardia and enhance the effects of pacing and defibrillation stimuli. In the description of these embodiments, reference is made to sensing a "symptom" indicative of a condition of the heart that may be treated by application of the present invention. For the purpose of the present invention, the term "symptom" is used broadly to encompass any sign or indication of such a condition that can be detected through direct or indirect sensing of physiological parameters.

An embodiment of the present invention comprises an implantable cardiac treatment/stimulation device designed to inhibit the conduction of spurious electrical signals in cardiac tissue without pacing. The technique applied in the implantable device comprises a cooling element for cooling cardiac tissue. Optionally, one or both of the cooling embodiments may be provided in combination with cathodal-only or biphasic stimulation of the cardiac tissue.

An embodiment of the present invention provides a method for inhibiting the conduction of spurious electrical impulses in cardiac tissue. The method comprises establishing a temperature conducive to inhibited conduction of electrical impulses for a targeted portion of the heart; and applying a temperature decrease to the targeted portion to maintain the established temperature. The temperature of the targeted portion is sensed. If the targeted portion has reached the established temperature, the application of the temperature decrease is ceased. If the targeted portion has not achieved the established temperature, application of the temperature decrease to the targeted portion continues.

The decrease in temperature of the cardiac tissue may be achieved through various means, including by way of example and not as a limitation, applying a cooling fluid to the cardiac tissue, electrically cooling the cardiac tissue, and mechanically cooling the cardiac tissue.

Another embodiment of the present invention provides methods for inhibiting the conduction of spurious electrical impulses in cardiac tissue. The method comprises sensing the onset of arrhythmia, determining the temperature of the cardiac tissue at the time of onset of arrhythmia, and applying a temperature decrease to the cardiac tissue. In another method, the functioning of the cardiac tissue is sensed. If the cardiac tissue reverts to sinus rhythm, the application of the temperature decrease is ceased. If the cardiac tissue has not reverted to sinus rhythm, the application of the temperature decrease to the cardiac tissue is continued.

The decrease in temperature of the cardiac tissue may be achieved through various means, including by way of example and not as a limitation, applying a cooling fluid to the cardiac tissue, electrically cooling the cardiac tissue, mechanically cooling the cardiac tissue, and cooling the cardiac tissue via an endothermic chemical reaction. Examples of cooling devices suitable for use in practicing the present invention are evaporative coolers, radiative coolers, chillers, thermal holdover devices (such as thermal storage units, with or without utilization of phase change phenomena), and gas expansion coolers. Cooling may be accomplished via a heat exchanger structure or via direct contact.

In another embodiment of the present invention, sensing the onset of arrhythmia comprises sensing a symptom indicative of arrhythmia. Various symptoms indicative of arrhythmia may be sensed, including by way of example and not as a limitation an electrical change within the heart, and a change in a measure of heart function.

In another embodiment of the present invention, a method for inhibiting the conduction of spurious electrical impulses in cardiac tissue further comprising applying a pacing pulse to cardiac tissue. Pacing may be accomplished by one or more electrodes in contact with cardiac tissue, or electrodes located in the blood pool of one or more of the heart chambers. In either method, the pacing pulse is applied to the one or more electrodes. The pacing pulse may be a cathodal electrical waveform or a biphasic electrical waveform comprising cathodal and anodal elements.

Another embodiment of the present invention provides methods for inhibiting the conduction of spurious electrical impulses in cardiac tissue. One or more portions of the heart affected by one or more reentry circuits is targeted. In an embodiment of the present invention, each of the one or more targeted portions is selected from the group consisting of a right anterior-lateral atrial surface, a left anterior-lateral atrial surface, a right postero-lateral atrial surfaces, and a left postero-lateral atrial surface. A heat-transfer operator is situated at each of one or more targeted portions of the heart. In an embodiment of the present invention, the heat-transfer operator is a Peltier cooler. The Peltier cooler may be electrically connected to a power source implanted in the patient's torso. In another embodiment of the present invention, the heat-transfer operator is a heat sink that is thermally coupled to a Peltier cooler implanted in a patient's torso. Optionally, the heat sink is thermally couple using a mechanical contact or a thermal transfer fluid.

A symptom associated with an arrhythmia is detected, and, in response to detection of the symptom, the heat is selectively transferred away from the targeted portion in the heart related to arrhythmia by absorbing heat into the heat-transfer operator situated at the targeted portion.

The symptom may be detected within the heart. The heat-transfer operator is activated in response to the detection of arrhythmia. Various symptoms may be detected, including by way of example and not as a limitation, an electrical change within the heart and a change in a measure of heart function.

Another method comprises sensing the functioning of the heart and, in the event the symptom associated with arrhythmia is not detected, ceasing transferring heat away from at least one of the targeted portions.

In another embodiment of the present invention, a method for inhibiting the conduction of spurious electrical impulses in cardiac tissue further comprising applying a pacing pulse to cardiac tissue. Pacing may be accomplished by one or more electrodes in contact with cardiac tissue, or electrodes located in the blood pool of one or more of the heart chambers. In either method, the pacing pulse is applied to the one or more electrodes. The pacing pulse may be a cathodal electrical waveform or a biphasic electrical waveform comprising cathodal and anodal elements.

In another embodiment of the present invention, a method for inhibiting the conduction of spurious electrical impulses in cardiac tissue comprises applying a pacing pulse to cardiac tissue. Pacing may be accomplished by one or more electrodes in contact with cardiac tissue, or electrodes located in the blood pool of one or more of the heart chambers. In either method, the pacing pulse is applied to the one or more electrodes. The pacing pulse may be a cathodal electrical waveform or a biphasic electrical waveform comprising cathodal and anodal elements.

In another exemplary embodiment of the present invention, a method for suppressing arrhythmia in a patient is provided. A heat-transfer operator is implanted at each of one or more targeted portions of a patient's heart. At least one heat-transfer operator is operated to cool at least one targeted portion of the heart, thereby suppressing the arrhythmia. In an embodiment of the present invention, the heat-transfer operator is a Peltier cooler implanted on one or more targeted portions each selected from the group consisting of a right anterior-lateral atrial surface, a left anterior-lateral atrial surface, a right postero-lateral atrial surfaces, and a left postero-lateral atrial surface. The Peltier cooler may be electrically connected to a power source implanted in the patient's torso. In another embodiment of the present invention, the heat-transfer operator is a heat sink implanted on one or more targeted portions each selected from the group consisting of a right anterior-lateral atrial surface, a left anterior-lateral atrial surface, a right postero-lateral atrial surfaces, and a left postero-lateral atrial surface that is thermally coupled to a Peltier cooler implanted in a patient's torso. Optionally, the heat sink is thermally couple using a mechanical contact or a thermal transfer fluid.

Another method for suppressing arrhythmia in a patient comprises implanting in the patient's heart at least one sensing-contact for sensing a symptom and connecting the sensing-contact to a power source that supplies power for the operation of the heat-transfer operator upon the sensing of a symptom. Various symptoms may be sensed, including by way of illustration and not as a limitation, an electrical change within the heart, and a measure of heart function.

In another embodiment of the present invention, the method for suppressing arrhythmia in a patient further comprises applying a pacing pulse to cardiac tissue. Pacing may be accomplished by one or more electrodes in contact with cardiac tissue, or electrodes located in the blood pool of one or more of the heart chambers. In either method, the pacing pulse is applied to the one or more electrodes. The pacing pulse may be a cathodal electrical waveform or a biphasic electrical waveform comprising cathodal and anodal elements.

In still another embodiment of the present invention, methods are provided for inhibiting the conduction of spurious electrical impulses in cardiac tissue. The onset of arrhythmia is sensed and the sensed arrhythmia evaluated. The temperature of the cardiac tissue at the time of onset of arrhythmia is also determined. Based on the evaluation of the sensed arrhythmia and cardiac tissue temperature, one or more remedial measures is selected from the group consisting of applying a temperature decrease to the cardiac tissue and applying a pacing pulse to the cardiac tissue. The selected remedial measure is applied. Optionally, the cardiac tissue function is sensed and if the cardiac tissue reverts to sinus rhythm, the application of the remedial measure ceases. Similarly, if the cardiac tissue does not revert to sinus rhythm, application of the remedial measure continues.

In still other embodiments of the present invention, apparatuses for inhibiting the conduction of spurious electrical impulses in cardiac tissue are provided. An apparatus comprises a sensing means for sensing the onset of arrhythmia and a cooling means responsive to the sensing means for applying a cooling stimulus to the cardiac tissue. An apparatus further comprises logic means for sensing when a sinus rhythm has been reestablished in the cardiac tissue and for halting the cooling stimulus in the event a sinus rhythm has been reestablished. Additional means are provided to continue the cooling stimulus in the event a sinus rhythm has not been reestablished.

Cooling means include, by way of illustration and not as a limitation, means for applying a cooling fluid to the cardiac tissue, an electrical cooling apparatus, and a mechanical cooling apparatus. Additionally, the sensing means may be adapted to sense a symptom associated with an arrhythmia. By way of illustration and not as a limitation, the symptom may be an electrical change within the heart and a measure of heart function.

Another apparatus of the present invention further comprises a cardiac stimulation generator and one or more electrodes in contact with cardiac tissue. The electrodes are connected to the cardiac stimulation generator, which is adapted to apply a pacing pulse as a cathodal electrical waveform or a biphasic waveform to the caridiac tissue. In an alternative embodiment of the present invention, the electrodes are in contact with the cardiac blood pool. Optionally, the cardiac stimulation generator is responsive to the sensing means.

Yet another apparatus of the present invention for inhibiting the conduction of spurious electrical impulses in cardiac tissue comprises a sensor for detecting a symptom associated with an arrhythmia. By way of illustration and not as a limitation, the symptom may be an electrical change within the heart, a measure of heart function, and a change indicative of an arrhythmia. A heat-transfer operator is situated at each of one or more targeted portions in the heart. In an embodiment of the present invention, the heat-transfer operator is a Peltier cooler. The Peltier cooler may be electrically connected to a power source implanted in the patient's torso. In another embodiment of the present invention, the heat-transfer operator is a heat sink that is thermally coupled to a Peltier cooler implanted in a patient's torso. Optionally, the heat sink is thermally couple using a mechanical contact or a thermal transfer fluid.

The heat-transfer operator at each of the one or more targeted portions is adapted to respond to the sensor to remove heat from the targeted portion served by that heat-transfer operator. The sensor may be located on the heat-transfer operator.

An apparatus further comprises logic means for sensing when a sinus rhythm has been reestablished in the cardiac tissue and for halting the cooling stimulus in the event a sinus rhythm has been reestablished. Additional means are provided to continue the cooling stimulus in the event a sinus rhythm has not been reestablished.

In another embodiment of the present invention, the apparatus further comprises a power source adapted to apply power to the sensor and to activate the heat-transfer operator upon detection of a symptom. Optionally, the power source stores sufficient energy to suppress arrhythmia in a patient for an extended period of time. Additionally, the power source automatically ceases to apply power to the heat-transfer operator after the one or more targeted portions are sufficiently cooled. In an embodiment of the present invention, the one or more targeted portions are sufficiently cooled when there is a subsidence of the symptom as detected by the sensing-contact. Alternatively, the one or more targeted portions are sufficiently cooled when each targeted portion reaches a predetermined temperature as measured by a thermacouple. In yet another alternative embodiment, the one or more targeted portions are sufficiently cooled when heat is transferred away from the one or more targeted portions for a programmed period of time.

In an embodiment of the present invention, each of the one or more targeted portions is selected from the group consisting of a right anterior-lateral atrial surface, a left anterior-lateral atrial surface, a right postero-lateral atrial surfaces, and a left postero-lateral atrial surface.

In another embodiment of present invention, the apparatus further comprises a cardiac stimulation generator and one or more electrodes in contact with cardiac tissue. The electrodes are connected to the cardiac stimulation generator, which is adapted to apply a pacing pulse as a cathodal electrical waveform or a biphasic waveform to the caridiac tissue. In an alternative embodiment of the present invention, the electrodes are in contact with the cardiac blood pool. Optionally, the cardiac stimulation generator is responsive to the sensing means.

Yet another apparatus of the present invention suppresses arrhythmia in a patient. The apparatus comprises a sensor for detecting a symptom associated with an arrhythmia. By way of illustration and not as a limitation, the symptom may be an electrical change within the heart, a measure of heart function, and a change indicative of an arrhythmia. A heat-transfer operator is situated at each of one or more targeted portions in the heart, In response to the detection of arrhythmia, the heat-transfer operator at each of the one or more targeted portions is adapted to transfer heat away from the targeted portion served by that heat-transfer operator. As result, each of the one or more targeted portions is cooled and the arrhythmia is suppressed.

In an embodiment of the present invention, the heat-transfer operator is a Peltier cooler. The Peltier cooler may be electrically connected to a power source implanted in the patient's torso. The power source is adapted to apply power to the sensor and to activate the heat-transfer operator upon the detection of a symptom. In another embodiment of the present invention, the heat-transfer operator is a heat sink that is thermally coupled to a Peltier cooler implanted in a patient's torso. Optionally, the heat sink is thermally couple using a mechanical contact or a thermal transfer fluid.

In yet another embodiment of the present invention, the one or more targeted portions is each selected from the group consisting of a right anterior-lateral atrial surface, a left anterior-lateral atrial surface, a right postero-lateral atrial surfaces, and a left postero-lateral atrial surface.

In another embodiment of the present invention, the apparatus further comprises a power source adapted to apply power to the sensor and to activate the heat-transfer operator upon detection of a symptom.

In another embodiment of present invention, the apparatus further comprises a cardiac stimulation generator and one or more electrodes in contact with cardiac tissue. The electrodes are connected to the cardiac stimulation generator, which is adapted to apply a pacing pulse as a cathodal electrical waveform or a biphasic waveform to the caridiac tissue. In an alternative embodiment of the present invention, the electrodes are in contact with the cardiac blood pool. Optionally, the cardiac stimulation generator is responsive to the sensor.

Figure 1:
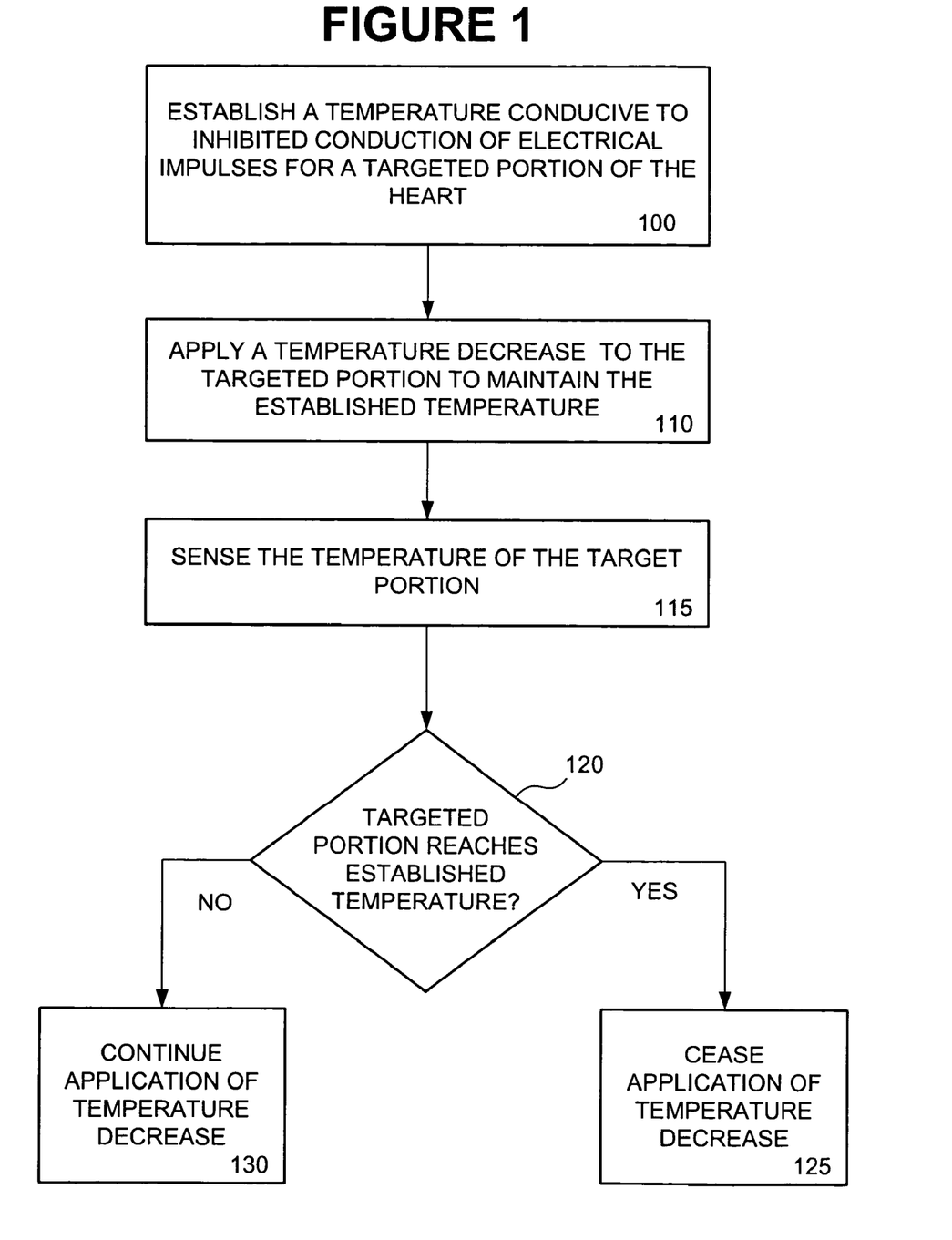
FIG. 1 illustrates a methodology for inhibiting the conduction of spurious electrical impulses in cardiac tissue according to embodiments of the present invention

FIG. 1 illustrates a methodology for inhibiting the conduction of spurious electrical impulses in cardiac tissue according to embodiments of the present invention. Referring to FIG. 1, a temperature conducive to inhibited conduction of electrical impulses is established for a targeted portion of the heart 100. A temperature decrease is applied to the targeted portion to maintain the established temperature 110. The temperature of the targeted portion is sensed 115 and a determination is made as to whether the targeted portion has reached the established temperature 120. If the targeted portion has reached the established temperature, the application of the temperature decrease is ceased 125. If the targeted portion has not achieved the established temperature, application of the temperature decrease to the targeted portion continues 130. While FIG. 1 illustrates a single targeted portion, the present invention is not so limited. One or more targeted portions may be identified and associated with an established temperature 120 without departing from the scope of the present invention.

The decrease in temperature of the cardiac tissue may be achieved through various means, including by way of example and not as a limitation, applying a cooling fluid to the cardiac tissue, electrically cooling the cardiac tissue, and mechanically cooling the cardiac tissue.

Figure 2:
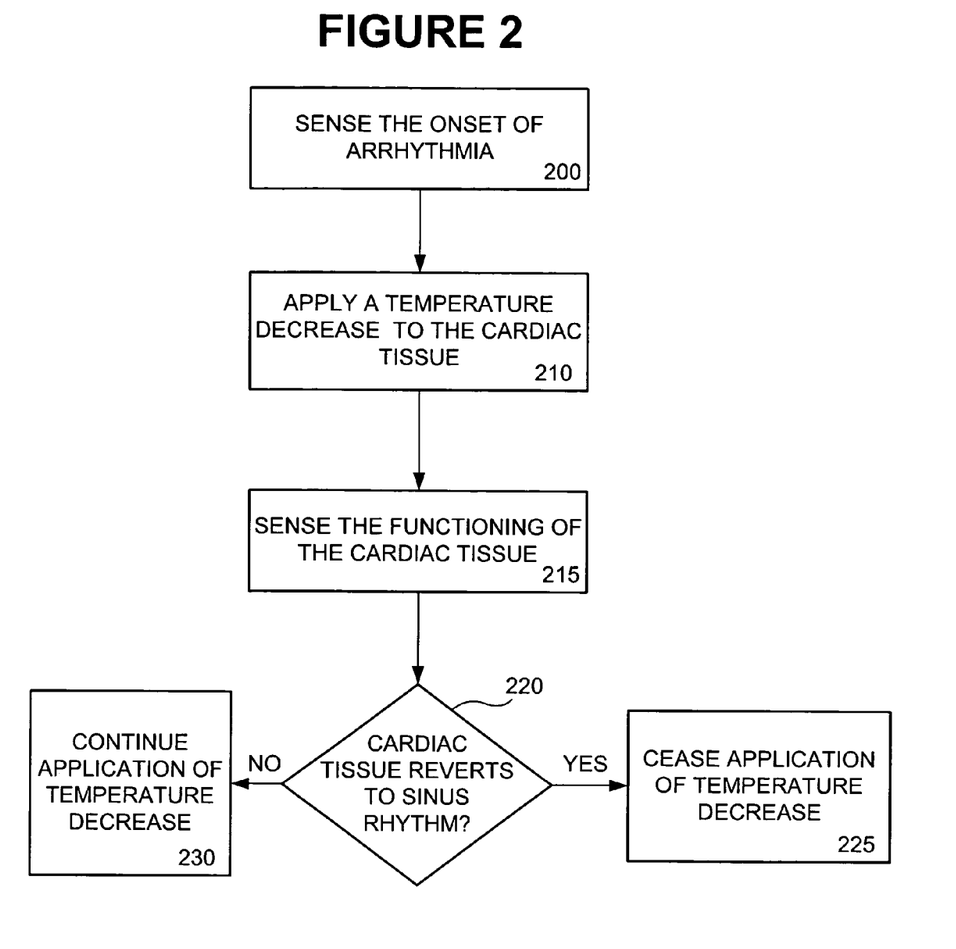
FIG. 2 illustrates a methodology for inhibiting the conduction of spurious electrical impulses in cardiac tissue by application of a temperature decrease to cardiac tissue according to embodiments of the present invention.

FIG. 2 illustrates a methodology for inhibiting the conduction of electrical spurious electrical impulses in cardiac tissue by application of a temperature decrease to cardiac tissue according to embodiments of the present invention. Referring to FIG. 2, the onset of arrhythmia is sensed 200 and a temperature decrease applied to cardiac tissue 210. The functioning of the cardiac tissue is sensed 215 and a determination is made as to whether the cardiac tissue has reverted to sinus rhythm 220. If the cardiac tissue has reverted to sinus rhythm, the application of a temperature decrease to the cardiac tissue is ceased 225. If the cardiac tissue has not reverted to sinus rhythm, the application of a temperature decrease to the cardiac tissue is continued 230.

Figure 3:
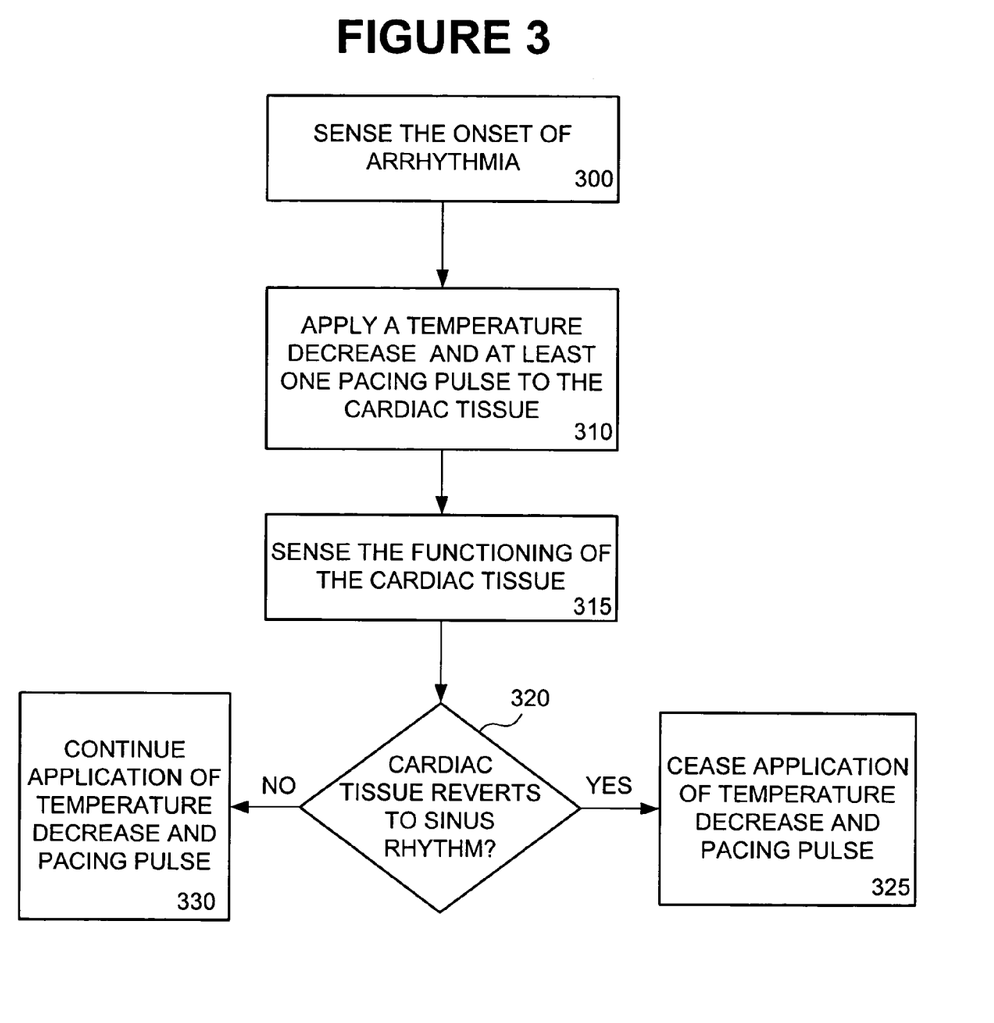
FIG. 3 illustrates a methodology for inhibiting the conduction of spurious electrical impulses in cardiac tissue by application of a temperature decrease and at least one pacing pulse to cardiac tissue according to embodiments of the present invention.

FIG. 3 illustrates a methodology for inhibiting the conduction of spurious electrical impulses in cardiac tissue by application of a temperature decrease and at least one pacing pulse to cardiac tissue according to embodiments of the present invention. Referring to FIG. 3, the onset of arrhythmia is sensed 300. At least one pacing pulse and a temperature decrease are applied to cardiac tissue 310. The functioning of the cardiac tissue is sensed 315 and a determination is made as to whether the cardiac tissue has reverted to sinus rhythm 320. If the cardiac tissue has reverted to sinus rhythm, the application of the at least one pacing pulse and a temperature decrease to the cardiac tissue is ceased 325. If the cardiac tissue has not reverted to sinus rhythm, the application of the at least one pacing pulse and a temperature decrease is continued 330. As previously described, a pacing pulse may be cathodal or biphasic and may be applied to the cardiac tissue through electrodes in contact with the blood pool of the heart or in contact with the cardiac tissue.

Figure 4:
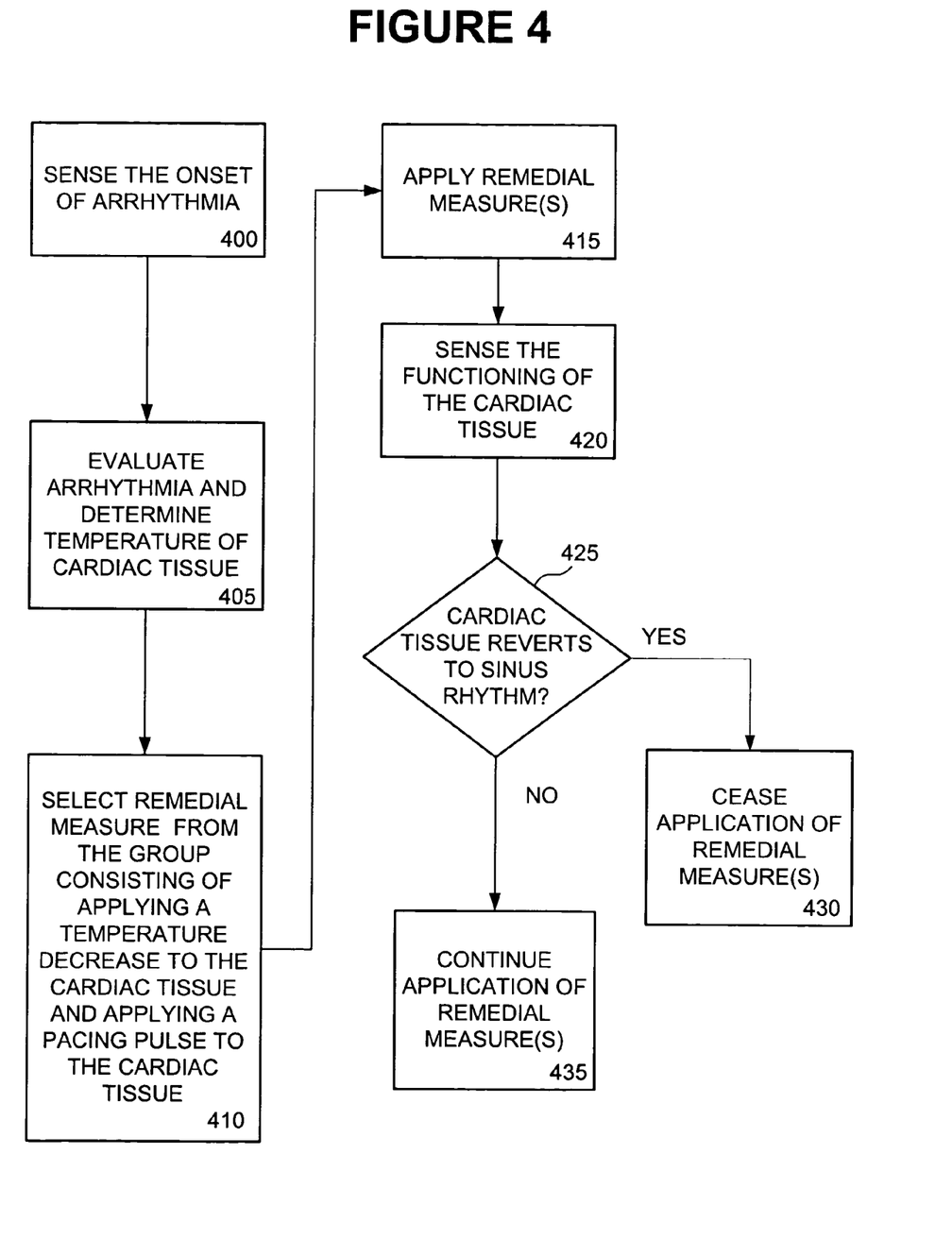
FIG. 4 illustrates a methodology for suppressing arrhythmia by selective application of a temperature decrease to a targeted portion of the heart and pacing pulses to cardiac tissue according to embodiments of the present invention.

FIG. 4 illustrates a methodology for suppressing arrhythmia by selective application of a temperature decrease to a targeted portion of the heart and pacing pulses to cardiac tissue according to embodiments of the present invention. Referring to FIG. 4, the onset of arrhythmia is sensed 400. The arrhythmia is evaluated and the temperature of the cardiac tissue is determined 405. Based on the evaluation of the sensed arrhythmia and cardiac tissue temperature, one or more remedial measures is selected from the group consisting of applying a temperature decrease to the cardiac tissue and applying a pacing pulse to the cardiac tissue 410. The selected remedial measure(s) is (are) applied to the cardiac tissue 415. The selective application of heart cooling and pacing pulses is determined by logic incorporated into a computer processor. In an embodiment of the present invention, the processor is located in the means that provides the pacing pulse. Alternatively, the processor is located in the means that provides the cooling function. In yet another embodiment of the present invention, the processor is a separate device. The functioning of the cardiac tissue is sensed 420 and a determination is made as to whether the cardiac tissue has reverted to sinus rhythm 425. If the cardiac tissue has reverted to sinus rhythm, the application of the selected remedial measure(s) ceases 430. If the cardiac tissue has not reverted to sinus rhythm, the application of the selected remedial measure(s) continues 435. In an alternate embodiment, the temperature of the cardiac tissue and the arrhythmia are reevaluated and one or more remedial measures are again selected.

As previously described, the pacing pulse may be cathodal or biphasic and may be applied to the cardiac tissue through electrodes in contact with the blood pool of the heart or in contact with the cardiac tissue.

Figure 5:
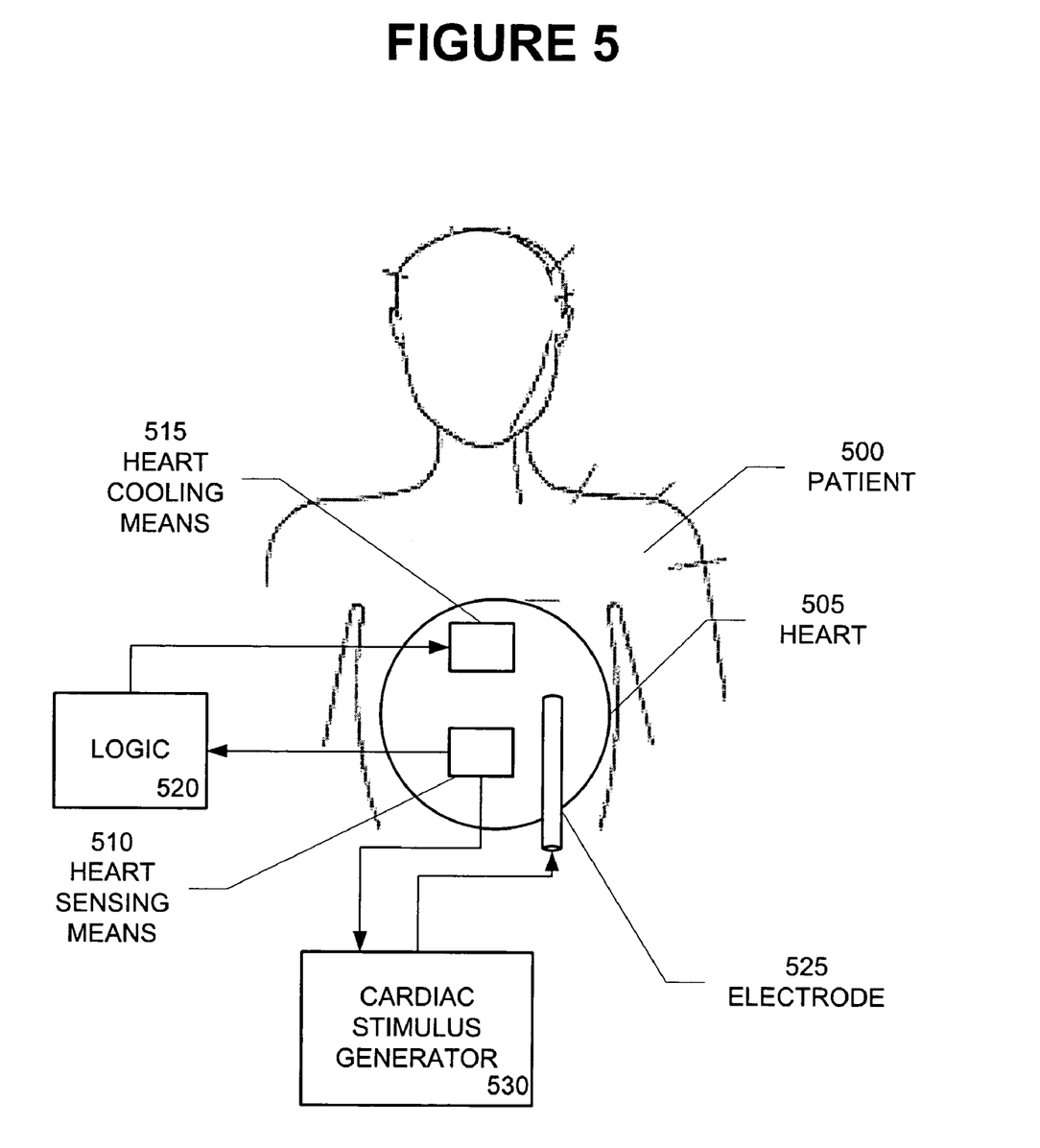
FIG. 5 illustrates an apparatus for inhibiting the conduction of electrical impulses in cardiac tissue by application of a temperature decrease to a targeted portion of the heart according to embodiments of the present invention.

FIG. 5 illustrates an apparatus for inhibiting the conduction of spurious electrical impulses in cardiac tissue by application of a temperature decrease to a targeted portion of the heart according to embodiments of the present invention. Referring to FIG. 5, a heart sensing means 510 and a heart cooling means 515 are applied to a heart 505 in a patient 500. In an embodiment of the present invention, heart sensing means 510 senses the onset of arrhythmia. In response to the heart sensing means 510, cooling is applied to the heart via heart cooling means 515. Logic 520 senses when a sinus rhythm has been reestablished in the cardiac tissue. If a sinus rhythm has been reestablished in the cardiac tissue, logic 520 halts the cooling stimulus to cooling means 515. If a sinus rhythm has not been reestablished in the cardiac tissue, logic 520 continues the cooling stimulus to cooling means 515.

In an embodiment of the present invention, heart cooling means 515 comprises a Peltier cooler. Such heat-transfer operators pass electricity through junctions between dissimilar metals. The atoms of the dissimilar metals have a difference in energy levels that results in a step between energy levels at each of the metals' junctions. As electricity is passed through the metals, the electrons of the metal with the lower energy level pass the first step as they flow to the metal with the higher energy level. In order to pass this step and continue the circuit, the electrons must absorb heat energy that causes the metal at the first junction to cool. At the opposite junction, where electrons travel from a high energy level to a low energy level they give off energy which results in an increase in temperature at that junction.

As will be appreciated by those skilled in the art, other cooling means may be utilized to perform the functions of the present invention without departing from its scope. By way of illustration and not as a limitation, heart cooling means 515 may be another device or system that absorbs heat from a specific area and accomplishes heat transfer through convection of fluids or conduction. Alternatively, cooling may be accomplished by a mechanical hydraulic system for pumping cooled fluid into a bladder on the surface of the atrium. The amount of cooling applied and the total temperature of the heart may be monitored through a "thermostat" function of the apparatus.

In another embodiment of the present invention, heart cooling means further comprises a heat sink thermally coupled to a heat-transfer operator, such as a Peltier cooler. The heat-transfer operator is electrically connected to a power source that supplies a current through the heat-transfer operator to affect heat transfer. The power source operates efficiently by powering off the heat-transfer operator supply when heat transfer is not needed. When heat transfer is desired, the power source can be activated to supply a DC current to the heat-transfer operator that will, in turn, activate heat transfer from the targeted portion through the temperature-contact to the cold junction of the heat-transfer operator.

In another embodiment of the present invention, the heat-transfer operator is responsive to the heart sensing means 510, which detects a symptom of arrhythmia. The symptoms detected by the heart sensing means may be electrical or physiological measures indicative of arrhythmia.

In yet another embodiment of the present invention, logic 520 determines a time for sufficient cooling the heart. The time necessary for sufficient cooling may be programmed into logic 520 or may be calculated by logic 520 based on information obtained from heart sensing means 510.

Referring again to FIG. 5, in another embodiment of the present invention, a cardiac stimulation generator 530 applies a pacing pulse to the cardiac tissue via electrode 525. While FIG. 5 illustrates a single electrode, the present invention is not so limited. As will be appreciated by those skilled in the art, multiple electrodes may be utilized without departing from the scope of the present invention. Additionally, electrode 525 may be placed in contact with the cardiac tissue or be located within a blood pool of the heart. Cardiac stimulation generator 530 is responsive to heart sensing means 510. The pacing pulse generated by cardiac stimulation generator 530 may be a cathodal electrical waveform or a biphasic electrical waveform comprising cathodal and anodal elements.

While the embodiments of the present invention have been directed to cooling cardiac tissue for the purpose of inhibiting the conduction of spurious electrical impulses, the present invention is not so limited. Spurious electrical signals affect other parts of the human body (e.g., the brain, skeletal muscles, pain receptors) that can be inhibited by cooling. As would be apparent to those skilled in the art, the embodiments of the present invention may be applied to inhibit spurious electrical signals of other parts of the body without departing from the scope of the present invention.

Systems and methods for inhibiting the conduction of spurious electrical impulses in cardiac tissue have been described. It will be understood by those skilled in the art of the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. A method for inhibiting the conduction of spurious electrical impulses in cardiac tissue comprising:
   sensing the onset of arrhythmia;
   determining a start temperature of the cardiac tissue at the time of onset of arrhythmia; and
   applying a temperature decrease to the cardiac tissue via a cooling means, the cooling means selected from the group consisting of: applying a cooling fluid to the cardiac tissue, electrically cooling the cardiac tissue, mechanically cooling the cardiac tissue, and chemically cooling the cardiac tissue using an endothermic chemical reaction; wherein the conduction of spurious electrical impulses in the cardiac tissue are inhibited.

2. The method for inhibiting the conduction of spurious electrical impulses in cardiac tissue of claim 1 further comprising:
   monitoring a current temperature of the cardiac tissue; and
   ceasing the application of the temperature decrease when the current temperature is less than or equal to a desired temperature.

3. A method for inhibiting the conduction of spurious electrical impulses in cardiac tissue comprising:
   sensing the onset of arrhythmia;
   determining a start temperature of the cardiac tissue at the time of onset of arrhythmia;
   applying a temperature decrease to the cardiac tissue; and
   applying a pacing pulse to the cardiac tissue, wherein the conduction of spurious electrical impulses in the cardiac tissue are inhibited.

4. The method for inhibiting the conduction of spurious electrical impulses in cardiac tissue of claim 3, wherein applying a pacing pulse to the heart comprises:
   planting an electrode in contact with cardiac tissue; and
   applying the pacing pulse to the cardiac tissue via the electrode.

5. The method for inhibiting the conduction of spurious electrical impulses in cardiac tissue of claim 4, wherein the pacing pulse is a cathodal electrical waveform.

6. The method for inhibiting the conduction of spurious electrical impulses in cardiac tissue of claim 4, wherein the pacing pulse is a biphasic electrical waveform.

7. The method for inhibiting the conduction of spurious electrical impulses in cardiac tissue of claim 3, wherein applying a pacing pulse to the heart comprises:
   locating an electrode in a cardiac blood pool; and
   applying the pacing pulse to the cardiac blood pool via the electrode.

8. The method for inhibiting the conduction of spurious electrical impulses in cardiac tissue of claim 7, wherein the pacing pulse is a cathodal electrical waveform.

9. The method for inhibiting the conduction of spurious electrical impulses in cardiac tissue of claim 7, wherein the pacing pulse is a biphasic electrical waveform.

10. The method for inhibiting the conduction of spurious electrical impulses in cardiac tissue of claim 3 further comprising:
    monitoring a current temperature of the cardiac tissue; and
    ceasing the application of the temperature decrease when the current temperature is less than or equal to a desired temperature.

11. A method for inhibiting the conduction of spurious electrical impulses in cardiac tissue comprising:
    detecting a symptom associated with an arrhythmia;
    determining a start temperature of the cardiac tissue at the time the symptom is detected;
    targeting a portion of the heart affected by a reentry circuit; and
    in response to detection of the symptom, transferring heat away from the targeted portion of the heart by absorbing heat into a Peltier cooler located at the targeted portion.

12. The method for inhibiting the conduction of electrical impulses in cardiac tissue of claim 11, wherein the Peltier cooler is electrically connected to a power source implanted in the patient's torso.

13. The method for inhibiting the conduction of electrical impulses in cardiac tissue of claim 11, wherein the targeted portion is selected from the group consisting of a right anterior-lateral atrial surface, a left anterior-lateral atrial surface, a right postero-lateral a,trial surfaces, and a left postero-lateral atrial surface.

14. A method for inhibiting the conduction of spurious electrical impulses in cardiac tissue comprising:
    detecting a symptom associated with an arrhythmia;
    determining a start temperature of the cardiac tissue at the time the symptom is detected;
    targeting a portion of the heart affected by a reentry circuit; and
    in response to detection of the symptom, transferring heat away from the targeted portion in the heart by absorbing heat into heat sink located at the targeted portion and thermally coupled to a Peltier cooler enclosed in a housing that is implanted in the patient's torso.

15. The method for inhibiting the conduction of electrical impulses in cardiac tissue of claim 14, wherein the Peltier cooler is electrically connected to a power source located within the housing.

16. The method for inhibiting the conduction of electrical impulses in cardiac tissue of claim 14, wherein the heat sink is coupled to the Peltier cooler though mechanical contact.

17. The method for inhibiting the conduction of electrical impulses in cardiac tissue of claim 14, wherein the heat sink is coupled to the Peltier cooler through a thermal transfer fluid.

18. The method for inhibiting the conduction of electrical impulses in cardiac tissue of claim 14, wherein the targeted portion is selected from the group consisting of a right anterior-lateral atrial surface, a left anterior-lateral atrial surface, a right postero-lateral atrial surfaces, and a left postero-lateral atrial surface.

19. A method for inhibiting the conduction of spurious electrical impulses in cardiac tissue comprising:
    detecting a symptom associated with an arrhythmia;
    determining a start temperature of the cardiac tissue at the time the symptom is detected;
    targeting a portion of the heart affected by a reentry circuit;
    in response to detection of the symptom, transferring heat away from the targeted portion in the bean by absorbing heat into a heat-transfer operator located at the targeted portion; and
    applying a pacing pulse to cardiac tissue.

20. The method for inhibiting the conduction of electrical impulses in cardiac tissue of claim 19, wherein applying a pacing pulse to the heart comprises:
    planting an electrode in contact with cardiac tissue; and
    applying the pacing pulse to the cardiac tissue via the electrode.

21. The method for inhibiting the conduction of electrical impulses in cardiac tissue of claim 20, wherein the pacing pulse is a cathodal electrical waveform.

22. The method for inhibiting the conduction of electrical impulses in cardiac tissue of claim 20, wherein the pacing pulse is a biphasic electrical waveform.

23. The method for inhibiting the conduction of electrical impulses in cardiac tissue of claim 19, wherein applying a pacing pulse to the heart comprises:
    locating an electrode in a cardiac blood pool; and
    applying the pacing pulse to the cardiac blood pool via the electrode.

24. The method for inhibiting the conduction of electrical impulses in cardiac tissue of claim 23, wherein the pacing pulse is a cathodal electrical waveform.

25. The method for inhibiting, the conduction of electrical impulses in cardiac tissue of claim 24, wherein the pacing pulse is a biphasic electrical waveform.

26. A method for suppressing arrhythmia in a patient comprising:
    implanting a heat-transfer operator in contact with a targeted portion of the patient's heart;
    suppressing the arrhythmia by operating a heat-transfer operator implanted at the targeted portion to cool the targeted portion of the heart;
    wherein implanting a heat-transfer operator in contact with the targeted portion of the patient's heart comprises implanting a Peltier cooler on the targeted portion,
    wherein the targeted portion is selected from the group consisting of a right anterior-lateral atrial surface, a left anterior-lateral atrial surface, a right postero-lateral atrial surfaces, and a left postero-lateral atrial surface; and
    applying a biphasic pulse to cardiac tissue, wherein the biphasic pulse comprises:
    a first stimulation phase with a first phase polarity, a first phase amplitude,
    a first phase shape and a first phase duration;
    a second stimulation phase with a polarity opposite to the first phase polarity, a second phase amplitude that is larger in absolute value than the first phase amplitude, a second phase shape and a second phase duration,
    wherein the first stimulation phase and the second stimulation phase are applied in sequence to cardiac tissue.

27. The method for suppressing arrhythmia in a patient of claim 26, wherein the Peltier cooler is electrically connected to a power source implanted in the patient's torso.

28. The method for suppressing arrhythmia in a patient of claim 26 further comprising:
monitoring a current temperature of the cardiac tissue; and
ceasing the application of the temperature decrease when the current temperature is less than or equal to a desired temperature.

29. A method for suppressing arrhythmia in a patient comprising:
implanting a heat-transfer operator in contact with a targeted portion of the patient's heart;
suppressing the arrhythmia by operating a heat-transfer operator implanted at the targeted portion to cool the targeted portion of the heart;
implanting a heat sink on the targeted portion, wherein the targeted portion is selected from the group consisting of a right anterior-lateral atrial surface, a left anterior-lateral atrial surface, a right postero-lateral atrial surfaces, and a left postero-lateral atrial surface;
thermally coupling the heat sink implanted on the targeted portion to a Peltier cooler enclosed in a housing that is implanted in the patient's torso; and
applying a biphasic pacing pulse to cardiac tissue, wherein the biphasic pulse comprises:
a first stimulation phase with a first phase polarity, a first phase amplitude,
a first phase shape and a first phase duration;
a second stimulation phase with a polarity opposite to the first phase polarity, a second phase amplitude that is larger in absolute value than the first phase amplitude, a second phase shape and a second phase duration,
wherein the first stimulation phase and the second stimulation phase are applied in sequence to the cardiac tissue.

30. The method for suppressing arrhythmia in a patient of claim 29, wherein the Peltier cooler is electrically connected to a power source located within the housing.

31. The method for suppressing arrhythmia in a patient of claim 29, wherein the heat sink is coupled to the Peltier cooler through mechanical contact.

32. The method for suppressing arrhythmia in a patient of claim 29, wherein the heat sink is coupled to the Peltier cooler through a thermal transfer fluid.

33. The method for suppressing arrhythmia in a patient of claim 26, wherein the method further comprises detecting a symptom associated with an arrhythmia.

34. The method for suppressing arrhythmia in a patient of claim 33, wherein detecting a symptom associated with the arrhythmia comprises detecting a symptom selected from the group consisting of a change in a measure of heart function and an electrical change within the heart.

35. The method for suppressing arrhythmia in a patient of claim 29 further comprising:
monitoring a current temperature of the cardiac tissue; and
ceasing the application of the temperature decrease when the current temperature is less than or equal to a desired temperature.

36. A method for suppressing arrhythmia in a patient Comprising:
implanting a heat-transfer operator in contact with a targeted portion of the patient's heart;
suppressing the arrhythmia by operating a heat-transfer operator implanted at the targeted portion to cool the targeted portion of the heart; and applying a biphasic pacing pulse to cardiac tissue, wherein the biphasic pulse comprises:
a first stimulation phase with a first phase polarity, a first phase amplitude,
a first phase shape and a first phase duration;
a second stimulation phase with a polarity opposite to the first phase polarity, a second phase amplitude that is larger in absolute value than the first phase amplitude, a second phase shape and a second phase duration,
wherein the first stimulation phase and the second stimulation phase are applied in sequence to cardiac tissue.

37. The method for suppressing arrhythmia in a patient of claim 36, wherein applying a pacing pulse to the heart comprises:
planting an electrode in contact with cardiac tissue; and
applying the biphasic pacing pulse to the cardiac tissue via the electrode.

38. The method for suppressing arrhythmia in a patient of claim 37, wherein the first phase polarity is positive.

39. The method for suppressing arrhythmia in a patient of claim 37, wherein the first phase amplitude is ramped from a baseline value to a second value.

40. The method for suppressing arrhythmia in a patient of claim 37, wherein applying a pacing pulse to the heart comprises:
locating an electrode in a cardiac blood pool; and
applying the pacing pulse to the cardiac blood pool via the electrode.

41. The method for suppressing arrhythmia in a patient of claim 40, wherein the wherein the first phase polarity is positive.

42. The method for suppressing arrhythmia in a patient of claim 41, wherein the first phase amplitude is ramped from a baseline value to a second value.

43. The method for suppressing arrhythmia in a patient of claim 36 further comprising:
monitoring a current temperature of the cardiac tissue; and
ceasing the application of the temperature decrease when the current temperature is less than or equal to a desired temperature.

44. A method for inhibiting the conduction of spurious electrical impulses in cardiac tissue comprising:
sensing the onset of arrhythmia;
evaluating the sensed arrhythmia;
determining a start temperature of the cardiac tissue at the time of onset of arrhythmia;
based on the evaluation of the sensed arrhythmia and the start temperature, selecting one or more remedial measures from the group consisting of applying a temperature decrease to the cardiac tissue and applying a pacing pulse to the cardiac tissue; and
applying the selected remedial measures.

45. The method for inhibiting the conduction of spurious electrical impulses in cardiac tissue of claim 44 further comprising:
sensing the cardiac tissue functioning; and
ceasing the application of the selected remedial measures if the cardiac tissue reverts to sinus rhythm.

46. The method for inhibiting the conduction of spurious electrical impulses in cardiac tissue of claim 44 further comprising:
sensing the cardiac tissue functioning; and continuing the application of the selected remedial measures if the cardiac tissue has not reverted to sinus rhythm.

47. The method for inhibiting the conduction of spurious electrical impulses in cardiac tissue of claim 44 further comprising:
sensing the cardiac tissue functioning; and
ceasing the application of the selected remedial measures if the cardiac tissue reverts to sinus rhythm.

48. The method for inhibiting the conduction of spurious electrical impulses in cardiac tissue of claim 44 further comprising:
sensing the cardiac tissue functioning;
if the cardiac tissue has not returned to sinus rhythm, selecting one or more continuing remedial measures from the group consisting of applying a temperature decrease to the cardiac tissue and applying a pacing pulse to the cardiac tissue; and
applying the selected one or more continuing remedial measures.

49. The method for inhibiting the conduction of spurious electrical impulses in cardiac tissue of claim 44 further comprising:
monitoring a current temperature of the cardiac tissue; and
ceasing the application of the temperature decrease when the current temperature is less than or equal to a desired temperature.

50. An apparatus far inhibiting the conduction of spurious electrical impulses in cardiac tissue comprising:
a sensing means for sensing the onset of arrhythmia
a means for determining a start temperature of the cardiac tissue at the time of onset of arrhythmia; and
a cooling means responsive to the sensing means for applying a cooling stimulus to the cardiac tissue;
wherein the cooling means is selected from the group consisting of a means for applying a cooling fluid to the cardiac tissue, an electrical cooling apparatus, a mechanical cooling apparatus, and an endothermic chemical reaction.

51. An apparatus for inhibiting the conduction of spurious electrical impulses in cardiac tissue comprising;
a sensing means for sensing the onset of arrhythmia;
a means for determining a start temperature of the cardiac tissue at the time of onset of arrhythmia;
a cooling means responsive to the sensing means for applying a cooling stimulus to the cardiac tissue;
a cardiac stimulation generator; and
an electrode in contact with cardiac tissue, wherein the electrode is connected to the cardiac stimulation generator,
wherein the cardiac stimulation generator is adapted to apply a pacing pulse to the cardiac tissue.

52. The apparatus of claim 51, wherein the cardiac Stimulation generator is responsive to the sensing means.

53. The apparatus of claim 52 further comprising:
a cardiac stimulation generator;
an electrode in contact with a cardiac blood pool, wherein the electrode is connected to the cardiac stimulation generator; and
wherein the cardiac stimulation generator is adapted to apply a pacing pulse to the cardiac blood pool.

54. The apparatus of claim 53, wherein the pacing pulse is a cathodal electrical waveform.

55. The apparatus of claim 54, wherein the pacing pulse is a biphasic electrical waveform.

56. The apparatus of claim 51, wherein the pacing pulse is a cathodal electrical waveform.

57. The apparatus of claim 51, wherein the pacing pulse is a biphasic electrical waveform.

58. A method for inhibiting the conduction of spurious electrical impulses in cardiac tissue comprising:
sensing the onset of arrhythmia;
detecting a start temperature of the cardiac tissue at the time of onset of the arrhythmia;
evaluating the sensed arrhythmia;
monitoring a cardiac tissue temperature;
using the evaluation of the sensed arrhythmia and the cardiac tissue temperature to select one or more remedial measures from the group consisting of applying a temperature decrease to the cardiac tissue and applying a pacing pulse to the cardiac tissue; and
applying the selected remedial measures.

* * * * *